US010464864B2

(12) United States Patent
Cao et al.

(10) Patent No.: US 10,464,864 B2
(45) Date of Patent: Nov. 5, 2019

(54) UPGRADING ETHANE-CONTAINING LIGHT PARAFFINS STREAMS

(71) Applicant: ExxonMobil Research and Engineering Company, Annandale, NJ (US)

(72) Inventors: Guang Cao, Princeton, NJ (US); Jihad Dakka, Whitehouse Station, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/834,209

(22) Filed: Dec. 7, 2017

(65) Prior Publication Data

US 2018/0170826 A1  Jun. 21, 2018

Related U.S. Application Data

(60) Provisional application No. 62/436,534, filed on Dec. 20, 2016, provisional application No. 62/436,542, filed on Dec. 20, 2016.

(51) Int. Cl.
| | |
|---|---|
| C07C 5/48 | (2006.01) |
| C07C 5/42 | (2006.01) |
| C07C 2/12 | (2006.01) |
| C07C 2/58 | (2006.01) |
| C07C 2/24 | (2006.01) |
| C10G 50/00 | (2006.01) |

(52) U.S. Cl.
CPC ............ *C07C 5/48* (2013.01); *C07C 2/12* (2013.01); *C07C 2/24* (2013.01); *C07C 2/58* (2013.01); *C10G 50/00* (2013.01); *C07C 2523/28* (2013.01); *C07C 2523/30* (2013.01); *C07C 2523/72* (2013.01); *C07C 2523/755* (2013.01); *C07C 2529/068* (2013.01); *C07C 2529/072* (2013.01); *C07C 2529/40* (2013.01); *C07C 2529/48* (2013.01); *C10G 2400/02* (2013.01); *Y02P 20/52* (2015.11)

(58) Field of Classification Search
CPC .................................................. C07C 5/48
USPC ......................................................... 585/330
See application file for complete search history.

(56) References Cited

U.S. PATENT DOCUMENTS

| | | | |
|---|---|---|---|
| 3,893,942 A | 7/1975 | Yang | |
| 4,250,346 A | 2/1981 | Young et al. | |
| 4,439,409 A | 3/1984 | Puppe et al. | |
| 4,568,790 A | 2/1986 | McCain | |
| 4,717,782 A * | 1/1988 | Garwood | C07C 2/12 585/255 |
| 5,236,575 A | 8/1993 | Bennett et al. | |
| 5,250,277 A | 10/1993 | Kresge et al. | |
| 5,362,697 A | 11/1994 | Fung et al. | |
| 5,608,133 A * | 3/1997 | Chang | B01J 21/06 585/502 |
| 5,780,703 A | 7/1998 | Chang et al. | |
| 6,756,030 B1 | 6/2004 | Rohde et al. | |
| 7,713,513 B2 | 5/2010 | Jan et al. | |
| 7,807,601 B2 | 10/2010 | Wang et al. | |
| 7,910,772 B2 | 3/2011 | Wang et al. | |
| 8,105,971 B2 | 1/2012 | Gaffney et al. | |
| 8,105,972 B2 | 1/2012 | Gaffney et al. | |
| 8,519,210 B2 | 8/2013 | Arnold et al. | |
| 9,409,156 B2 | 8/2016 | Sanchez Valente et al. | |
| 2007/0249793 A1 | 10/2007 | Vanderbilt et al. | |
| 2008/0058574 A1 | 3/2008 | Tonkovich et al. | |
| 2010/0249480 A1 * | 9/2010 | Nicholas | C07C 2/10 585/518 |
| 2010/0255985 A1 * | 10/2010 | Gaffney | B01J 23/002 502/312 |
| 2010/0256432 A1 | 10/2010 | Arnold et al. | |
| 2011/0245571 A1 | 10/2011 | Kustov et al. | |
| 2012/0016171 A1 | 1/2012 | Kustov et al. | |
| 2015/0065769 A1 | 3/2015 | Henao et al. | |
| 2015/0175907 A1 | 6/2015 | Yao et al. | |
| 2017/0210685 A1 * | 7/2017 | Simanzhenkov | B01J 38/30 |

FOREIGN PATENT DOCUMENTS

| | | |
|---|---|---|
| EP | 922017 B1 | 9/2003 |
| WO | 9717290 A1 | 5/1997 |

OTHER PUBLICATIONS

Ebinger, C. K., Avasarala, G. "Natural Gas Liquids", (2013); pp. 2-15. (Year: 2013).*
The International Search Report and Written Opinion of PCT/US2017/065008 dated Feb. 28, 2018.
The International Search Report and Written Opinion of PCT/US2017/065007 dated Apr. 26, 2018.
Cavani et al., "Oxidative dehydrogenation of ethane and propane: How far from commercial implementation?", Catalysis Today, 2007, 127, 113-131.
Cavani et al., "Oxidative dehydrogenation of ethane and propane: How far from commercial implementation?", Catalysis Today, Sep. 2007, pp. 113-131, vol. 127, Issues 1-4, Science Direct, Elsevier.
Thorsteinson et al., "The Oxidative Dehydrogenation of Ethane over Catalyst Containing Mixed Oxide of Molybdenum and Vanadium", Journal of Catalysis, Mar. 1978, pp. 116-132, vol. 52, Science Direct, Elsevier.
Botella et al., "Selective oxidative dehydrogenation of ethane on MoVTeNbO mixed metal oxide catalysts", Journal of Catalysis, Jul. 25, 2004, pp. 428-438, iss. 225, Science Direct, Elsevier.

* cited by examiner

*Primary Examiner* — Youngsul Jeong
(74) *Attorney, Agent, or Firm* — Priya G. Prasad

(57) ABSTRACT

In a process for upgrading an ethane-containing $C_{5-}$ paraffin stream, the paraffin stream is contacted with an oxygen containing gas in the presence of a selective oxidation catalyst under conditions to selectively oxidize at least part of the ethane in the paraffin stream and produce a first product stream comprising ethylene. At least part of the first product stream is then with an oligomerization catalyst under conditions to oligomerize at least part of the ethylene and produce a second product stream comprising gasoline and/or distillate boiling range hydrocarbons. Gasoline and/or distillate boiling range hydrocarbons are then recovered from the second product stream and at least a part of any residual $C_{5-}$ paraffin stream is recycled to the selective oxidation step.

18 Claims, No Drawings

UPGRADING ETHANE-CONTAINING LIGHT PARAFFINS STREAMS

CROSS-REFERENCE TO RELATED APPLICATIONS

This application claims the benefit of U.S. Provisional Application No. 62/436,534, filed on Dec. 20, 2016, the entire contents of which are incorporated herein by reference.

This application also claims the benefit of related U.S. Provisional Application No. 62/436,542, filed on Dec. 20, 2016, the entire contents of which are incorporated herein by reference.

FIELD

The present disclosure relates to upgrading ethane-containing light paraffin ($C_{5-}$) streams, particularly natural gas liquid streams.

BACKGROUND

The supply of natural gas liquid (NGL) in North America has become abundant because of the shale gas boom. This provides an opportunity to use NGL as a low cost feedstock for the production of transportation fuels and chemicals. Greater supply of shale oil also poses a challenge in meeting gasoline octane requirements, since shale oil-sourced naphthas inherently have low octane values. Efficient conversion of NGL to high octane gasoline and/or high cetane diesel fuel can help alleviate these problems.

At present, commercially-proven processes for upgrading light paraffins are centered around dehydrogenation. For example, the $C_3$ and $C_4$ Oleflex™ processes, produce propylene and iso-butene by dehydrogenation of propane and iso-butane feedstock, respectively, in a series of radial flow reactors. In addition, the Cyclar™ process converts liquefied petroleum gas (LPG) directly into liquid aromatics by dehydrocyclodimerization, which involves the sequential dehydrogenation of $C_3$ and/or $C_4$ alkanes to olefins, oligomerization of the olefins, cyclization to naphthenes and dehydrogenation of naphthenes to corresponding aromatics.

However, these processes have so far only been used for generating higher value chemical feedstocks because of the high capital and operating costs involved. In addition, they do not address the oversupply of ethane. There is therefore a need to develop a cost effective process for converting ethane in mixed light paraffin ($C_{5-}$) streams to liquid fuels.

An alternative process for converting alkanes to alkenes is by selective oxidation, in which the alkane is catalytically dehydrogenated in the presence of oxygen. The process is also called oxidative dehydrogenation (ODH) and can be carried out at lower reaction temperatures than reductive dehydrogenation processes discussed above, and without the same problem of coke formation. For example, U.S. Pat. No. 8,519,210 discloses a process for the oxidative dehydrogenation of gaseous hydrocarbons, particularly ethane, to olefins, particularly ethylene. The process comprises contacting an ethane feed and an oxygen-containing gas in the presence of at least one of water and steam and an oxidative dehydrogenation catalyst comprising $Mo_aV_bNb_cY_dTe_eO_n$ wherein Y=Sb or Ni; a=1.0; b=0.05 to 1.0; c=0.001 to 1.0; d=0.001 to 1.0; e=0.001 to 0.5; and n is determined by the oxidation states of the other elements.

It is also known from, for example, U.S. Pat. Nos. 7,807,601 and 7,910,772, that light alkanes, especially propane can be selectively oxidized into unsaturated carboxylic acids, such as acrylic acid, in the presence of mixed-metal oxide catalysts having the formula $Mo_aV_bNb_cTe_dSb_eO_f$ wherein, when a=1, b=0.01 to 1.0, c=0.01 to 1.0, d=0.01 to 1.0, e=0.01 to 1.0, and f is dependent upon the oxidation state of the other elements.

A recent overview of the development of the selective oxidation of ethane and propane can be found in an article entitled "Oxidative dehydrogenation of ethane and propane: How far from commercial implementation?" by F. Cavani, N. Ballarini, and A. Cericola in *Catalysis Today*, vol. 127, Issues 1-4, 2007, pages 113-131.

However, although the selective oxidation of light alkanes has been extensively studied, the focus of the studies has been on the production of chemicals and chemical intermediates and, as reported in the Cavani et al. article, significant commercial utility has yet to be demonstrated.

SUMMARY

According to the present disclosure, it has now been appreciated that the combination of selective oxidation with oligomerization of the resultant olefins can be used to upgrade ethane-containing light paraffin ($C_{5-}$) streams, particularly natural gas liquid streams, to high octane gasoline and/or high cetane distillate. Such a combination achieves the joint goals of providing an economically attractive route for utilization of the increasing supply of natural gas liquid and addressing the lower octane and cetane values inherent in the increased use of shale oils as gasoline and distillate components.

Thus, in one aspect, the present disclosure resides in a process for upgrading an ethane-containing $C_{5-}$ paraffin stream, the process comprising:

(a) contacting the paraffin stream with an oxygen containing gas in the presence of a selective oxidation catalyst under conditions to selectively oxidize at least part of the ethane in the paraffin stream and produce a first product stream comprising ethylene; and (b) contacting at least part of the first product stream with at least one oligomerization catalyst under conditions to oligomerize at least part of the ethylene and produce a second product stream comprising gasoline and/or distillate boiling range hydrocarbons; and (c) recovering gasoline and/or distillate boiling range hydrocarbons from the second product stream and recycling at least a part of the residual $C_{5-}$ paraffin stream to the contacting (a).

DETAILED DESCRIPTION

For the purpose of this description and appended claims, the following terms are defined. The term "$C_n$" hydrocarbon wherein n is a positive integer, e.g., 1, 2, 3, 4, or 5, means a hydrocarbon having n number of carbon atom(s) per molecule. The term "$C_{n+}$" hydrocarbon wherein n is a positive integer, e.g., 1, 2, 3, 4, or 5, means a hydrocarbon having at least n number of carbon atom(s) per molecule. The term "$C_{n-}$" hydrocarbon wherein n is a positive integer, e.g., 1, 2, 3, 4, or 5, means a hydrocarbon having no more than n number of carbon atom(s) per molecule. The term "hydrocarbon" encompasses mixtures of hydrocarbon having different values of n. As used herein, the numbering scheme for the groups of the Periodic Table of the Elements is as disclosed in Chemical and Engineering News, 63(5), 27 (1985).

Described herein is a multi-step process for upgrading an ethane-containing light paraffin ($C_{5-}$) stream, particularly a natural gas liquid stream or fraction thereof, to gasoline and/or distillate boiling range hydrocarbons. As a first step, the ethane-containing light paraffin ($C_{5-}$) stream is reacted with an oxygen containing gas in the presence of a selective oxidation catalyst under conditions to convert at least part of the ethane to ethylene. At least part of the resultant ethylene is then oligomerized in a single stage or in multiple stages to produce the desired gasoline and/or distillate boiling range hydrocarbons. Residual $C_{5-}$ paraffins can be separated from the selective oxidation effluent and/or the oligomerization effluent and recycled back to the selective oxidation step.

Feedstock

The present process can be used to upgrade any ethane-containing light paraffin ($C_{5-}$) feedstock, but is particularly effective for upgrading natural gas liquid (NGL) streams and fractions thereof. NGL is a mixture of ethane and lesser quantities of propane, butanes and pentanes remaining after demethanization of natural gas. In most cases, the as-produced natural gas is initially subjected to multiple pre-treatment steps to remove condensate, water, nitrogen and reactive gaseous impurities, such as hydrogen sulfide and carbon oxides, before being fed to the demethanizer. In addition, before being used in the present process, the NGL can be treated, for example by fractionation, to remove part or all of the $C_{3+}$ hydrocarbons.

Preferred ethane-containing light paraffin ($C_{5-}$) streams useful in the present process contain at least 80 wt %, such as at least 85 wt %. for example at least 90 wt %, such as at least 95 wt %, even up to 100 wt %, ethane; less than 20 wt %, such as less than 15 wt %, for example less than 10 wt %, such as less than 5 wt % methane and/or less than 20 wt %, such as less than 15 wt %, for example less than 10 wt %, such as less than 5 wt % propane. To avoid excessive separation costs, most light paraffin streams employed in the present process will contain at least 0.5 wt % methane and/or at least 0.5 wt % propane.

Ethane Oxydehydrogenation

Any catalyst effective for the oxydehydrogenation of ethane in a $C_{5-}$ mixed paraffin stream to produce ethylene can be used in the present process. The effectiveness of the catalyst is usually primarily determined by two parameters: the activity of the catalyst for ethane conversion, and selectivity (efficiency) of the conversion to ethylene rather than acetic acid. Suitable oxydehydrogenation catalysts with a desirable combination of activity and selectivity are frequently mixed metal oxides, especially mixed oxides of molybdenum and vanadium, optionally with one or more other metal oxides. One such preferred oxide is niobium oxide.

For example, the article entitled "The Oxidative Dehydrogenation of Ethane over Catalyst Containing Mixed Oxide of Molybdenum and Vanadium" by E. M. Thorsteinson, T. P. Wilson, F. G. Young and P. H. Kasai, Journal of Catalysis 52, pp. 116-132 (1978) discloses that mixed oxide catalysts containing molybdenum and vanadium together with another transition metal oxide (Ti, Cr, Mn, Fe, Co, Ni, Nb, Ta, or Ce) are active at temperatures as low as 200° C. for the oxydehydrogenation of ethane to ethylene.

U.S. Pat. No. 4,250,346, the entire contents of which are incorporated herein by reference, discloses catalytic oxydehydrogenation of ethane to ethylene at temperatures less than 550° C. in which the catalyst is a calcined composition comprising the elements Mo, X, and Y in the ratio:

$$Mo_aX_bY_c$$

wherein: X=Cr, Mn, Nb, Ta, Ti, V, and/or W; Y=Bi, Ce, Co, Cu, Fe, K, Mg, Ni, P, Pb, Sb, Si, Sn, Tl, and/or U; a=1; b=0.05 to 1.0 and c=0 to 2.

U.S. Pat. No. 4,568,790, the entire contents of which are incorporated herein by reference, discloses process for converting ethane to ethylene by catalytically oxydehydrogenating ethane exothermically at a temperature of less than 450° C. in the gas phase using a calcined catalyst containing:

$$Mo_aV_bNb_cSb_d$$

wherein a=0.5 to 0.9, b=0.1 to 0.4, c=0.001 to 0.2 and d=0.001 to 0.1.

U.S. Pat. No. 7,910,772, the entire contents of which are incorporated herein by reference, discloses a catalyst for the oxidation of an alkane, alkene or mixtures thereof and including a mixed-metal oxide having the formula $Mo_aV_b$-$Nb_cTe_dSb_eO_f$ wherein, when a=1, b=0.01 to 1.0, c=0.01 to 1.0, d=0.01 to 1.0, e=0.01 to 1.0, and f is dependent upon the oxidation state of the other elements, the catalyst further characterized by having at least two crystal phases, the first crystal phase being an orthorhombic M1 phase and the second crystal phase being a pseudo-hexagonal M2 phase, the orthorhombic M1 phase present in an amount between greater than 60 weight percent to less than 90 weight percent.

U. S. Patent Application Publication Nos. 2011/0245571A1 and U.S. 2012/0016171A1, to Nova Chemicals International S.A., disclose a process for the preparation of a catalyst for the oxidative dehydrogenation of ethane, with a relatively high yield to ethylene reporting selectivity to ethylene higher than 90% with productivity in the range 2,500 g ethylene per hour and kg of catalyst. The catalyst employed is a tellurium-containing solid with as general formula $V_xMo_yNb_zTe_mMe_nO_p$, wherein Me is a metal belonging to the group Ta, Ti, W, Hf, Zr and Sb, or a mixture of them. The entire contents of these patent documents are incorporated herein by reference.

U.S. Patent Application Publication No. 2010/0256432A1, assigned to Lummus Novolent GMBH/Lummus Technology Inc., and U.S. Pat. No. 8,105,971 B2 assigned to Lummus Technology Inc., disclose a high performance catalyst for the oxidative dehydrogenation of ethane to ethylene. Over this catalytic system represented by $Mo_{1.0}V_{0.29}Nb_{0.17}Sb_{0.01}Te_{0.125}O_x$, ethane conversion reportedly reach values of up to 81% with an ethylene selectivity of 89% when reaction is conducted at 360° C. The entire contents of these patent documents are incorporated herein by reference.

U.S. Pat. No. 9,409,156, the entire contents of which are incorporated herein by reference, discloses the oxidative dehydrogenation of light paraffins, such as ethane, at moderate temperatures (<500° C.) to produce ethylene without the formation of side products, such as acetic acid and/or other oxygenated hydrocarbons, using a tellurium-free, multimetallic catalyst possessing orthorhombic M1 phase having the formula:

$$MoV_hSb_iA_jO_x$$

wherein A represents Nb, W, Ga, Bi, Sn, Cu, Ti, Fe, Co, Ni, Cr, Zr, rare earth metals or rare earth alkaline metals or mixtures of thereof, h and i, respectively, are each between 0.001 and 4.0, 0≤j≤2.0, the ratio i/h is between 0.3 and 10.0, and x represents the number determined by and consistent with the valence requirements of the other elements present in the multimetallic mixed oxide.

Any or all of the above mixed metal oxide catalyst compositions may be used in the ethane oxidative dehydrogenation step of the present process.

The mixed metal oxide catalyst is preferably prepared from a solution of soluble compounds (salts, complexes or other compounds) of each of the desired elements. The solution is preferably an aqueous system having a pH of 1 to 7, and preferably 2 to 6. The solution of the element containing compounds is prepared by dissolving sufficient quantities of soluble compounds of each of the elements, so as to provide the desired gram-atom ratios of the elements. To the extent possible the selected compounds of the various elements should be mutually soluble. Where any of the selected compounds of such elements are not mutually soluble with the other compounds, they can be added last to the solution system. The catalyst composition is then prepared by removing the water or other solvent from the mixture of the compounds in the solution system, such as by evaporation. The dried mixture may then be calcined by being heated at about 220 to 550° C. in air or oxygen for ½ to 24 hours to produce the final catalyst.

The mixed metal oxide catalyst can be used with or without a support. Suitable supports include silica, aluminum oxide, silicon carbide, zirconia, titania and mixtures thereof. When used on a support, the supported catalyst usually comprises about 10 to 50 weight % of the mixed metal oxide catalyst composition, with the remainder being the support.

Where the catalyst is to be used on a support, the compounds of the desired elements are deposited on a particulate porous support by immersing the support individually or collectively in a solution of each of the compounds, evaporating off the major portion of the solvent, and then drying the system at about 80 to 220° C. for 2 to 60 hours. Again the dried composition may then be calcined by being heated at about 220 to 550° C. in air or oxygen for ½ to 24 hours to produce the final catalyst.

In some cases, it may be desirable that one or more of the metal components in the mixed metal oxide catalyst should be slightly reduced below its highest possible oxidation state. This may be accomplished by thermal treatment of the catalyst in the presence of reducing agents such as $NH_3$ or organic reducing agents, such as the organic complexing agents, which are introduced into the solution systems from which the catalysts are prepared. The catalyst may also be reduced in the reactors in which the oxidation reaction is to be conducted by the passage of hydrogen or hydrocarbon reducing agents such as ethane, ethylene, or propylene through the catalyst bed.

The oxydehydrogenation reaction is conducted by contacting the ethane-containing light paraffin ($C_{5-}$) with any oxygen containing gas, such as air, in the presence of one or more mixed metal oxide catalysts as described above under conditions effective to selectively oxidize at least part of the ethane to produce ethylene. Suitable conditions include a temperature from 200° C. to 700° C., such as from 300 to 550° C. and a pressure from 100 kPa-a to 6895 kPa-a, such as from 100 to 5000 kPa-a. The reaction can be conducted in any suitable reactor, such as a fixed bed reactor or fluidized bed reactor.

The amount of oxygen added to the light paraffin ($C_{5-}$) feed is not critical but generally is selected such that the total feed to the oxydehydrogenation reaction is from 0.01 to 0.7 mole, such as from 0.1 to 0.6 mole of molecular oxygen (as pure oxygen or in the form of air) per mole of ethane in the feed. Since the reaction is exothermic, diluents can also be supplied to the reaction to moderate heat generation. Suitable diluents include water, nitrogen, helium, $CO_2$, and methane. It will be appreciated that water is an inherent by-product of the reaction.

By suitable selection of the catalyst and the reaction conditions, the oxidative dehydrogenation step can be conducted so as to selectively convert at least 50%, such as at least 60%, such as at least 70%, such as at least 80%, even as much as 90%, of the ethane in the feed to ethylene. Similarly, any propane and/or butane in the feed will be at least partly converted to propylene and butenes.

In addition to $C_{2+}$ olefins and co-produced water, the product of the oxidative dehydrogenation step may contain various organic oxygenates, for example carboxylic acids, such as acetic acid and acrylic acid; alcohols such as methanol and ethanol; aldehydes, such as formaldehyde, acetaldehyde, propionaldehyde, and acrylic aldehyde; esters, such as ethyl acetate and propane acetate and ketones, such as acetone. The product may also contain unreacted $C_{5-}$ hydrocarbons, as well as inert impurities present in the initial feedstock, such as $N_2$ and $CO_2$.

The product of the oxidative dehydrogenation step may be fed to the next stage in the process, namely ethylene oligomerization, without intermediate separation or may initially be subjected to one or more separation steps, for example, to remove unreacted $C_{5-}$ hydrocarbons for recycle to the dehydrogenation step or to recover valuable organic oxygenates, such as acetic acid and acrylic acid. Generally, however, intermediate separation is avoided since propene and higher olefins as well as many organic oxygenates can be converted to gasoline and/or distillate boiling range hydrocarbons in the oligomerization process.

Ethylene Oligomerization

Oligomerization of at least part of the ethylene component in the oxidative dehydrogenation effluent to produce gasoline and/or distillate boiling range hydrocarbons may be achieved by contacting the ethylene with one or more oligomerization catalysts in one or multiple stages.

In one embodiment, the oligomerization catalyst employed in at least one oligomerization stage comprises at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

Other suitable oligomerization catalysts comprise one or more large pore molecular sieves having a Constraint Index less than 2. Suitable large pore molecular sieves include zeolite beta, zeolite Y, Ultrastable Y (USY), Ultrahydrophobic Y (UHP-Y), Dealuminized Y (Deal Y), mordenite, ZSM-3, ZSM-4, ZSM-14, ZSM-18, ZSM-20 and mixtures thereof. Zeolite ZSM-3 is described in U.S. Pat. No. 3,415,736. Zeolite ZSM-4 is described in U.S. Pat. No. 4,021,947. Zeolite ZSM-14 is described in U.S. Pat. No. 3,923,636. Zeolite ZSM-18 is described in U.S. Pat. No. 3,950,496. Zeolite ZSM-20 is described in U.S. Pat. No. 3,972,983. Zeolite Beta is described in U.S. Pat. Nos. 3,308,069, and Re. No. 28,341. Low sodium Ultrastable Y molecular sieve (USY) is described in U.S. Pat. Nos. 3,293,192 and 3,449,070. Ultrahydrophobic Y (UHP-Y) is described in U.S. Pat. No. 4,401,556. Dealuminized Y zeolite (Deal Y) may be prepared by the method found in U.S. Pat. No. 3,442,795.

Zeolite Y and mordenite are naturally occurring materials but are also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Other suitable oligomerization catalysts comprise at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), UZM-8HS (described in U.S. Pat. No. 7,713,513) and mixtures thereof.

Generally, the molecular sieves described above are employed in the oligomerization catalyst as an aluminosilicate material having a silica to alumina molar ratio of at least 10, such as at least 25 to 100.

Preferred molecular sieves for use in the oligomerization reaction are those having a Constraint Index of 2-12 as described above, especially ZSM-5 and more particularly ZSM-5 having a homogeneous crystal size of <0.05 micron and a relatively high activity (alumina content) characterized by a $SiO_2/Al_2O_3$ molar ratio of around 50:1 or less.

The above molecular sieves may be employed in their acid forms, ion exchanged or impregnated with one or more suitable metals, such as Ga, Pd, Zn, Ni, Co and/or other metals of Periodic Groups 3 to 14. The molecular sieve may include a hydrogenation-dehydrogenation component (sometimes referred to as a hydrogenation component) which is generally one or more metals of Groups 5, 6 and 8 to 13 of the Periodic Table, especially aromatization metals such as Ga, Pd, etc. Useful hydrogenation components include the noble metals of Groups 9 to 11, especially platinum, gold, silver, rhenium, and rhodium. The catalyst material may include two or more catalytic components, such as metallic oligomerization component (e.g., ionic $Ni^{+2}$ and a shape-selective medium pore acidic oligomerization catalyst, such as ZSM-5 zeolite) which components may be present in admixture or combined in a unitary bifunctional solid particle.

The above molecular sieves may be used as the oligomerization catalyst without any binder or matrix, i.e., in so-called self-bound form. Alternatively, the molecular sieve may be composited with another material which is resistant to the temperatures and other conditions employed in the oligomerization reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

Oligomerization over the molecular sieves described above may be conducted over a wide range of temperatures and pressures, for example at temperatures from about 20° C. to 300° C. (preferably 50° C. to 200° C.) and pressures from ambient to about 5500 kPa (preferably about 250 to 2900 kPa). Within these ranges, higher severity conditions generally favor ethylene conversion and the production of gasoline ($C_5$-$C_{10}$) boiling-range products, whereas less severe conditions favor production of heavier distillate boiling-range products at the expense of ethylene conversion activity. Thus, in some embodiments, the oligomerization may be conducted in two or more stages, with one stage being conducted at higher severity conditions to produce olefinic gasoline and part or all of the gasoline being fed to a later oligomerization stage to produce distillate.

In some embodiments, the oligomerization over the molecular sieves described above may be preceded by, or occur simultaneously with, an ethylene dimerization step, in which part or all of the oxidative dehydrogenation product is contacted with a metal dimerization catalyst under conditions effective to convert ethylene to $C_{4+}$ olefins, especially 1-butene. In this respect, the term "dimerization" is used in the present specification to mean a specific case of oligomerization so that the broader term "oligomerization" is intended to include dimerization. The term oligomerization is also intended to processes in which the oligomerization is accompanied by cyclization to produce aromatic and non-aromatic cyclic olefins as well as non-cyclic linear or branched $C_{4+}$ olefins.

Suitable ethylene dimerization catalysts comprise one or more metals or compounds thereof selected from the group consisting of nickel, manganese, iron and copper deposited on a suitable support, such as silica. Where ethylene dimerization occurs simultaneously with oligomerization, the support may be one or more of the molecular sieves described above, especially ZSM-5.

Other suitable ethylene dimerization/oligomerization catalysts include mixed metal oxides containing, such as, as an oxide of a Group 4 metal, for example, Zr, and oxide of a Group 6 metal, such as W, optionally together with one or more oxides of Group 7 to 11 metals, such as Fe, Cu, Mn and Ce. A description of the production of such mixed metal oxides and their use in olefin oligomerization can be found in U.S. Pat. No. 5,608,133, the entire contents of which are incorporated herein by reference.

The oligomerization reaction can be conducted in any suitable reactor or series of reactors, including one or more fixed bed reactors, moving bed reactors and/or fluidized bed reactors.

Depending on the catalyst(s) and the reaction conditions employed, the effluent from the oligomerization reaction will contain gasoline and/or distillate boiling range hydrocarbons, together with unreacted ethylene and/or $C_{4+}$ olefins and potentially water, unreacted $C_{5-}$ hydrocarbons, organic oxygenates from the oxidative dehydrogenation reaction. In any event, the oligomerization effluent can be fed to a separation system, such as a distillation train, where gasoline and/or distillate boiling range hydrocarbons may be recovered, while the unreacted ethylene and/or $C_{4+}$ olefins can be separated for recycle to the oligomerization step, and unreacted $C_{5-}$ paraffins can be separated for recycle to the oxidative dehydrogenation step.

In some embodiments, isoparaffins and aromatic compounds can be cofed with the $C_{2+}$ olefins to the oligomerization reactor(s) so that some of the ethylene and, if present, propene and butenes, can react with the isoparaffin to generate alkylate, or can alkylate benzene to generate high octane product and also chemicals. In the case of cofeeding isoparaffins, the presence of propene/butenes in the feed is particularly advantageous in that it speeds up alkylation of the isoparaffins with the ethylene.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for upgrading an ethane-containing $C_5$-paraffin stream, the process comprising:
   (a) contacting the ethane-containing $C_5$-paraffin stream, wherein the ethane-containing $C_5$-paraffin stream comprises at least about 80 wt % ethane and less than about 20 wt % methane, propane, butane, and pentane, with an oxygen containing gas in the presence of a selective oxidation catalyst under conditions to selectively oxidize at least part of the ethane in the $C_5$-paraffin stream and produce a first product stream comprising ethylene and oxygenates selected from carboxylic acids and esters thereof, alcohols, aldehydes, ketones and mixtures thereof;
   (b) contacting the first product stream which contains ethylene and oxygenates selected from carboxylic acids and esters thereof, alcohols, aldehydes, ketones and mixtures thereof with at least one oligomerization catalyst, without intermediate separation, under conditions to oligomerize at least part of the ethylene and produce a second product stream comprising gasoline and/or distillate boiling range hydrocarbons and a residual $C_5$-paraffin stream; and
   (c) recovering the gasoline boiling range hydrocarbons and/or distillate boiling range hydrocarbons from the second product stream and recycling at least a part of the residual $C_5$- paraffin stream of the second product stream to the contacting step (a).

2. The process of claim 1, wherein the ethane-containing $C_5$-paraffin stream comprises ethane and propane.

3. The process of claim 1, wherein the ethane-containing $C_5$-paraffin stream comprises a natural gas liquid containing less than 20 wt % methane.

4. The process of claim 1, where the ethane-containing $C_5$-paraffin stream comprises less than 20 wt % propane.

5. The process of claim 1, wherein the selective oxidation catalyst comprises a mixed metal oxide.

6. The process of claim 5, wherein the mixed metal oxide is a mixed metal oxide of at least molybdenum and vanadium.

7. The process of claim 6, wherein the mixed metal oxide is a mixed oxide of at least molybdenum, vanadium, and niobium.

8. The process of claim 1, wherein the conditions in the contacting step (a) include a temperature from 200° C. to 700° C. and a pressure from 100 kPa-a to 6895 kPa-a.

9. The process of claim 1, wherein at least 50% of the ethane selectively oxidized in the contacting step (a) is converted to ethylene.

10. The process of claim 1, wherein the oligomerization catalyst comprises a molecular sieve.

11. The process of claim 10, wherein the molecular sieve has a Constraint Index of 1-12.

12. The process of claim 10, wherein the molecular sieve is selected from the group consisting of ZSM-5, ZSM-11, ZSM-12, ZSM-22, ZSM-23, ZSM-35, and ZSM-48.

13. The process of claim 10, wherein the molecular sieve comprises ZSM-5.

14. The process of claim 10, wherein the oligomerization catalyst further comprises a hydrogenation-dehydrogenation component.

15. The process of claim 14, wherein the hydrogenation-dehydrogenation component comprises at least one of Ga, Pt, Pd, Zn, Ni, and Co or a compound thereof.

16. The process of claim 1, wherein the oligomerization catalyst comprises a mixed metal oxide.

17. The process of claim 16, wherein the mixed metal oxide is a mixed metal oxide of at least zirconium and tungsten.

18. The process of claim 1, wherein the conditions in the contacting step (b) include a temperature from 300° C. to 550° C. and a pressure from 100 kPa-a to 5000 kPa-a.

* * * * *